United States Patent
Ball et al.

(10) Patent No.: US 6,945,976 B2
(45) Date of Patent: Sep. 20, 2005

(54) METHOD AND APPARATUS FOR RESECTING BONE FROM AN ULNA IN PREPARATION FOR PROSTHETIC IMPLANTATION

(75) Inventors: Robert J. Ball, Winona Lake, IN (US); Ian A. Trail, Worsley (GB); John K. Stanley, Wigan (GB)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/396,763

(22) Filed: Mar. 25, 2003

(65) Prior Publication Data

US 2003/0187451 A1 Oct. 2, 2003

Related U.S. Application Data

(60) Provisional application No. 60/368,787, filed on Mar. 29, 2002.

(51) Int. Cl.[7] .................................................. A61F 5/00
(52) U.S. Cl. .............................. 606/87; 606/80; 606/86
(58) Field of Search .............................. 606/80, 86, 87, 606/88

(56) References Cited

U.S. PATENT DOCUMENTS

| | | | |
|---|---|---|---|
| 4,624,250 A | | 11/1986 | Saunders et al. |
| 4,718,414 A | | 1/1988 | Saunders et al. |
| 4,893,619 A | * | 1/1990 | Dale et al. ................... 606/87 |
| 5,030,237 A | * | 7/1991 | Sorbie et al. ............. 623/20.11 |
| 5,108,396 A | * | 4/1992 | Lackey et al. ................ 606/62 |
| 5,597,379 A | | 1/1997 | Haines et al. |
| 5,779,709 A | * | 7/1998 | Harris et al. .................. 606/87 |

FOREIGN PATENT DOCUMENTS

| | | | |
|---|---|---|---|
| GB | 2331016 | * 12/1999 | ................... 606/87 |
| WO | WO 96/36284 | 11/1996 | |

OTHER PUBLICATIONS

Brochure (4 pages): Coonrad/Morrey Total Elbow prosthesis, *More Than Fifteen Years of Clinical Sucess*, Zimmer: © 1999, 2000.
Brochure (2 pages): Solar Upper Extremity System, *Linked Semi–Constrained Total Elbow system*, Stryker Howmedia Osteonics; © 1999.

* cited by examiner

*Primary Examiner*—Pedro Philogene

(57) ABSTRACT

A bone resection guide, particularly for an ulna, utilizes anatomical reference points of the ulna to establish an optimal position for a prosthesis. The bone resection guide provides a guiding instrument that allows a surgeon to remove only bone that needs to be removed for precise placement of the end prosthesis. A method of resecting bone from the ulna in preparation of prosthetic implantation using the bone resection guide matches an elbow axis finder with a particular size of an ulna fossa of the patient. Once matched, a sized resection template, directly related to the shape of the prosthesis, is used as a resection guide. Incorporated into the bone resection guide are known anthropometric qualities when providing resection surfaces. This enhances the probable position of the implant.

27 Claims, 11 Drawing Sheets

METHOD AND APPARATUS FOR RESECTING BONE FROM AN ULNA IN PREPARATION FOR PROSTHETIC IMPLANTATION

This application claims the benefit of U.S. Provisional Application Ser. No. 60/368,787, filed Mar. 29, 2002.

TECHNICAL FIELD OF THE INVENTION

The present invention relates to surgical devices particularly bone resection devices and, more particularly, to a surgical device and method of use for bone resection of the proximal ulna.

BACKGROUND OF THE INVENTION

A common problem in the orthopaedic industry is the need for accurate bone resection prior to implantation of a prosthesis, particularly of prosthetic joints. Appropriate positioning of the prosthesis has been shown in many cases to be a leading factor in long term stability of such prosthetic joints. This is true with respect to all types of prosthetic joints. The industry, however, has relatively neglected the ulna at the elbow joint.

A current standard of practice is to perform bone resection by hand without guidance of any kind, regardless of implant type. With respect to total elbow arthroplasty (TEA), loosening of the ulnar stem of the elbow prosthesis is a commonly reported complication. This complication raises questions related to surgical technique and its relationship to the complication.

As indicated, little work has been done specifically for the ulna in the area of designing precision surgical techniques for resection of the ulna bone and implant (prosthesis) positioning. A current and primary benchmark for arthroplasty for the past twenty years has been the Coonrad-Morrey prosthesis from Zimmer of Warsaw, Ind. The Coonrad-Morrey system, however, provides very little in terms of instrumentation for determining and positioning the implant relative to existing anatomy of a patient. One device for assistance in resection of the ulna for a TEA is the Solar Elbow™ from Stryker Howmedica Osteonics of Kalamazoo, Mich. The Solar Elbow™ provides with its instrumentation a device designed to assist in resection of the ulna to a shape complementing the implant. The Solar Elbow™ provides a template shaped to complement the implant that is held up to the bone and which is used to cut along. One problem with the Solar Elbow™ resection device is that there are no ties or reference to existing anatomy.

In U.S. Pat. No. 4,624,250 issued on Nov. 25, 1986 and U.S. Pat. No. 4,718,414 issued on Jan. 12, 1988 to Saunders et al., there is disclosed an instrument for elbow surface replacement arthroplasty (the "Saunders instrument"). The Saunders instrument and method of use bases resection of an ulna for elbow arthroplasty on the patient's humeral anatomy, particularly the condyles of the humerus. Particularly, Saunders uses the condyles of the humerus to establish a center of rotation for the humerus and relates such back to the ulna for resection thereof. Several problems, however, exist with the Saunders instrument and method of use. One problem is that there is no method for accounting for soft tissue balance. Resection is made from the anatomical center of the humerus with little consideration of the ulna. Another problem is that many cases exist in elbow arthroplasty in which the condyles of the humerus have been fractured or otherwise rendered useless, and thus cannot be used as a reference.

What is thus needed is a bone resection guide and/or method of use that utilizes the ulna as a reference for resection of the ulna.

What is thus further needed is a bone resection guide and/or method of use that allows resection of an ulna in a manner that allows precise placement of a final prosthesis or implant.

SUMMARY OF THE INVENTION

The subject invention is a bone resection guide or jig and/or a method or procedure of use in the resection of bone. Particularly, the subject invention is a bone resection guide or jig and/or a procedure of use for resection of bone of an ulna in preparation of a prosthetic implant (prosthesis).

In one form, the subject invention provides a method of resecting bone from an ulna in preparation of prosthetic implantation. The method includes the steps of: (a) creating a reference axis of natural elbow rotation of a patient with respect to an ulna of a patient; (b) selecting a resection template from one of a plurality of dimensions of resection templates; (c) providing the selected resection template to and with respect to the created reference axis of natural elbow rotation; and (d) resecting a portion of the ulna according to the selected resection template.

In another form, the subject invention provides a method of resecting bone from an ulna in preparation of prosthetic implantation. The method includes the steps of: (a) placing a selected mock trochlea into a trochlear notch of an ulna of a patient; (b) temporarily fixing the mock trochlea in the trochlear notch of the ulna; (c) placing a selected resection template onto the mock trochlea; and (d) resecting bone from the ulna according to the resection template.

In yet another form, the subject invention provides a bone resection guide for an ulna. The bone resection guide includes a frame, a guide block, and a mock trochlea holder. The guide block is adjustably carried by the frame and is operative to contact an olecrannon of an ulna of a patient. The mock trochlea holder is adjustably carried by the frame and is operative to temporarily retain a selected mock trochlea in a trochlear notch of the ulna of the patient.

The subject invention utilizes the existing anatomy (i.e. "boney landmarks") of an ulna to determine an appropriate location for an implant. The subject invention incorporates known qualities of the ulnar anatomy therein and into the position of the final implant. Further, the subject invention offers a surgeon a bone conserving approach, as well as an easy replication of the resection surface for further bone removal. Additionally, the subject invention complements the final implant or prosthesis particularly taking into account the center of rotation positions available through multiple sizes of ulnar bearings. Still further, the existing center of elbow rotation is approximated, allowing better balancing of soft tissue, thus leading to possibility of greater range of motion. Finally, the subject invention is low profile, thus requiring minimal incision sizes.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

Figure 1:
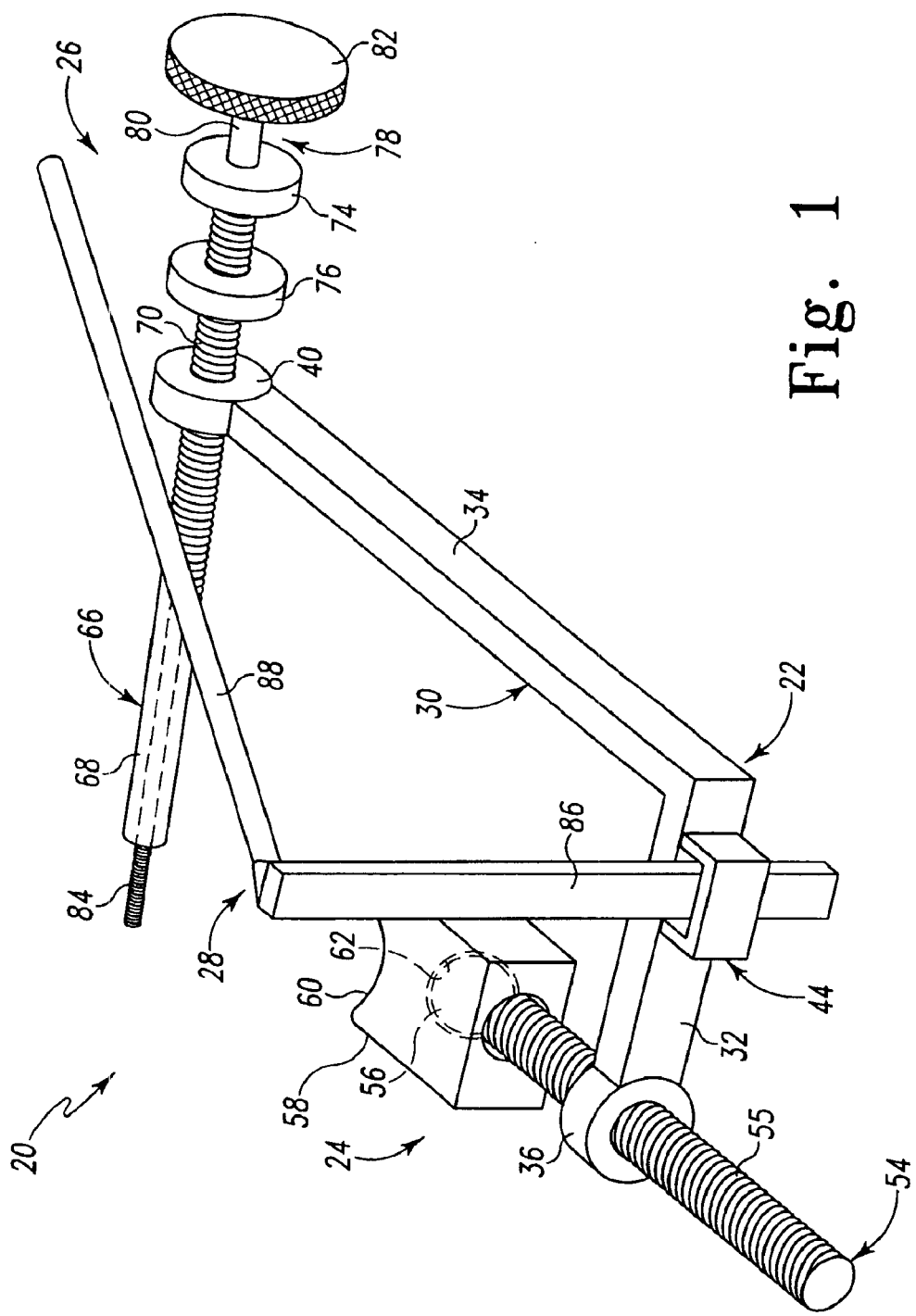
FIG. 1 is a perspective view of an exemplary bone resection guide or jig in accordance with the principles of the subject invention.

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention.

Referring now to FIG. 1 there is shown an exemplary embodiment of a surgical device, particularly a bone resection/resector guide or jig, generally designated 20 (hereinafter, collectively "bone resection guide"). The bone resection guide 20 is configured, adapted or operative to allow a surgeon to determine a proper and/or appropriate resection area or portion of an ulna and allow resection of the determined proper/appropriate resection area particularly in preparation of a prosthetic implant (i.e. an elbow prosthesis/prosthetic component).

The resection guide 20 has an exemplary resection guide frame assembly 22, an exemplary resection guide block assembly 24, an exemplary resection spool/mock trochlea retention and adjustment assembly 26, and an exemplary bone alignment/axis finder/locator assembly 28. Each assembly is preferably manufactured from a suitable material such as a metal, for steel, stainless steel, an aluminum alloy, or a polymeric material, unless specified otherwise. Other material or materials may be used as appropriate for the industry and/or for such surgical instruments.

The exemplary resection guide frame assembly 22 provides a main frame or support for the other components (assemblies) of the subject bone resection guide 20. As such, the subject resection guide frame assembly 22 may be configured differently than that shown without departing from the concept and such is contemplated. The resection guide frame assembly 22 supports the resection guide block assembly 24, the resection guide block assembly 24, the resection spool/mock trochlea retention and adjustment assembly 26, and the humeral bone alignment/axis finder/locator assembly 28. Particularly, the resection guide block assembly 24, the resection spool/mock trochlea retention and adjustment assembly 26, and the bone alignment/axis finder/locator assembly 28 are all adjustably and/or removably supported or retained on or by the resection guide frame assembly 22.

Figure 2:
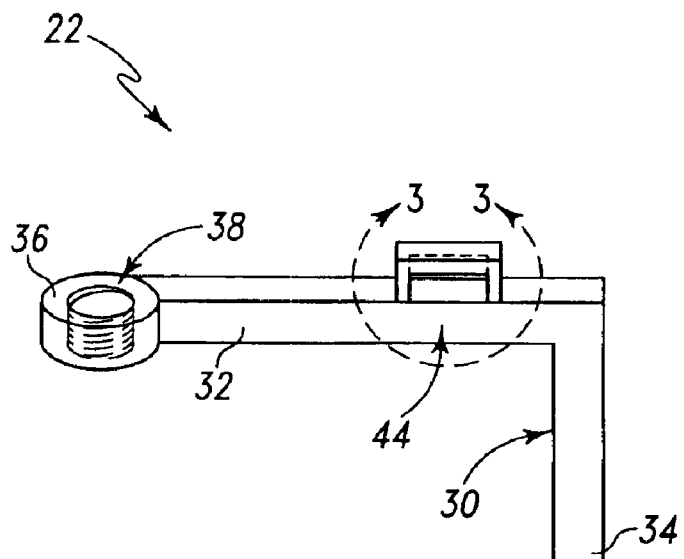
FIG. 2 is a perspective view of a guide frame for the exemplary bone resection guide of FIG. 1.

With additional reference to FIG. 2, the exemplary resection guide frame assembly 22 will be described with greater particularity. The resection guide frame assembly 22 includes a guide frame 30 that comprises a first leg, arm or the like 32 and a second leg, arm or the like 34. It should be appreciated that the nomenclature "first" and "second" are arbitrary and thus may be interchanged without consequence. The first and second legs 32 and 34 are joined at respective ends thereof essentially perpendicular to form a backwards "L". The first and second legs 32 and 24 are shown as bars, but may be rods or other-shaped members. The first leg 32 has an eyelet or holder 36 on one end thereof that is distal from the joining end/point of the first and second legs 32 and 34. The eyelet 36 has a threaded bore 38. As described below in greater detail and shown in FIG. 1, the threaded bore 38 threadedly receives a component of the resection guide block assembly 24. The second leg 34 has an eyelet or holder 40 on one end thereof that is distal from the joining end/point of the first and second legs 32 and 34. The eyelet 40 has a threaded bore 42. As described below in greater detail and shown in FIG. 1, the threaded bore 38 threadedly receives a component of the resection spool/mock trochlea retention and adjustment assembly 26.

Figure 3:
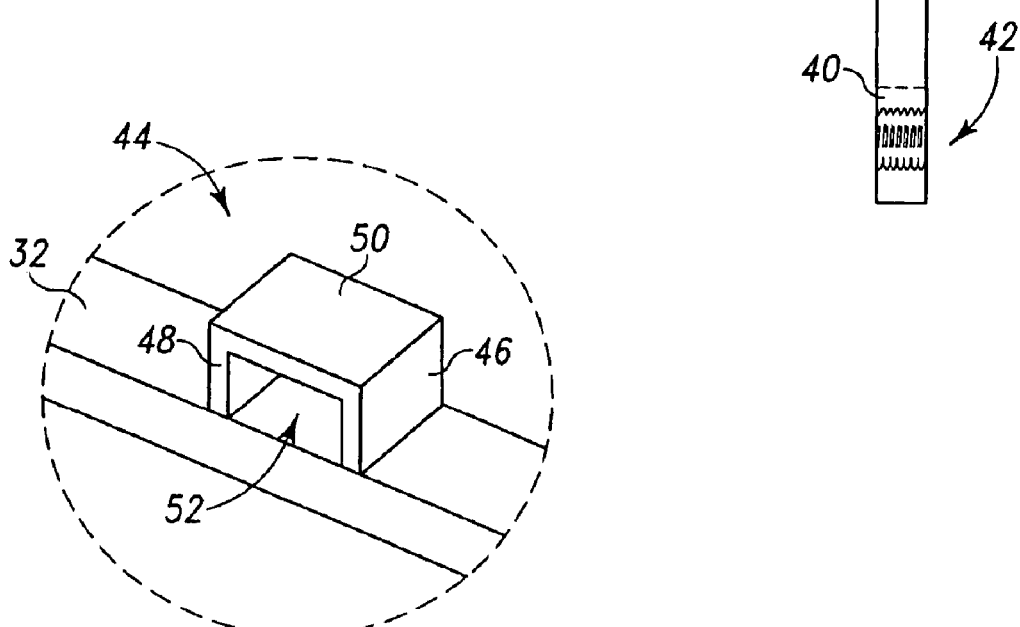
FIG. 3 is an enlarged perspective view of a portion of the guide frame taken along circle 3—3 of FIG. 2.

The guide frame 30 also includes a retention frame 44 that is positioned on the first leg 32. With additional reference to FIG. 3, the retention frame 44 includes a first wall or member 46 that is situated essentially perpendicular to a top surface of the first leg 32 and a second wall or member 48 that is situated essentially perpendicular to the top surface of the first leg 32 and spaced from the first wall 46. It should be appreciated that the nomenclature "first" and "second" are arbitrary and thus may be interchanged without consequence. The retention frame 44 also includes a top wall or member 50 that spans from the first wall 46 to the second wall 48. As such, the top wall 50 is essentially parallel to the top surface of the first leg 32. The walls 46, 48, and 50 define an opening 52 that is configured to retain a component of the humeral bone alignment/axis finder/locator assembly 28 (see FIG. 1). As such, the opening 52 is configured in like manner to the component of the bone alignment/axis finder/locator assembly 28 in order to receive and/or accommodate the component. The opening 52 may thus be configured differently in correspondence to the shape of the component of the bone alignment/axis finder/locator assembly 28.

Figure 4:
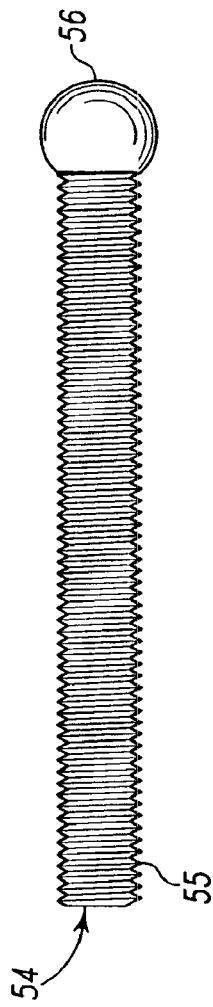
FIG. 4 is an enlarged plan view of a guide stem of the exemplary bone resection guide of FIG. 1.

Referring back to FIG. 1, the resection guide block assembly 24 of the resection guide 20 will be discussed. The resection guide block assembly 24 is configured, adapted and/or operative to contact the ulna and particularly the posterior aspect of the olecranon of the ulna when the bone resection guide 20 is installed. The resection guide block assembly 24 includes a guide stem 54 and a guide block 58 carried by the guide stem 54. The guide stem 54 is adjustable with respect to the guide frame 30, particularly with respect to the first leg 32. With additional reference to FIG. 4, the guide stem 54 is shown. The guide stem 54 includes threads 55 and a knob, sphere, rotundity, or the like 56 at one end thereof. The threads 55 preferably extend the length of the guide stem 54. The knob 56 is preferably smooth about its face or outer surface.

Figure 8:
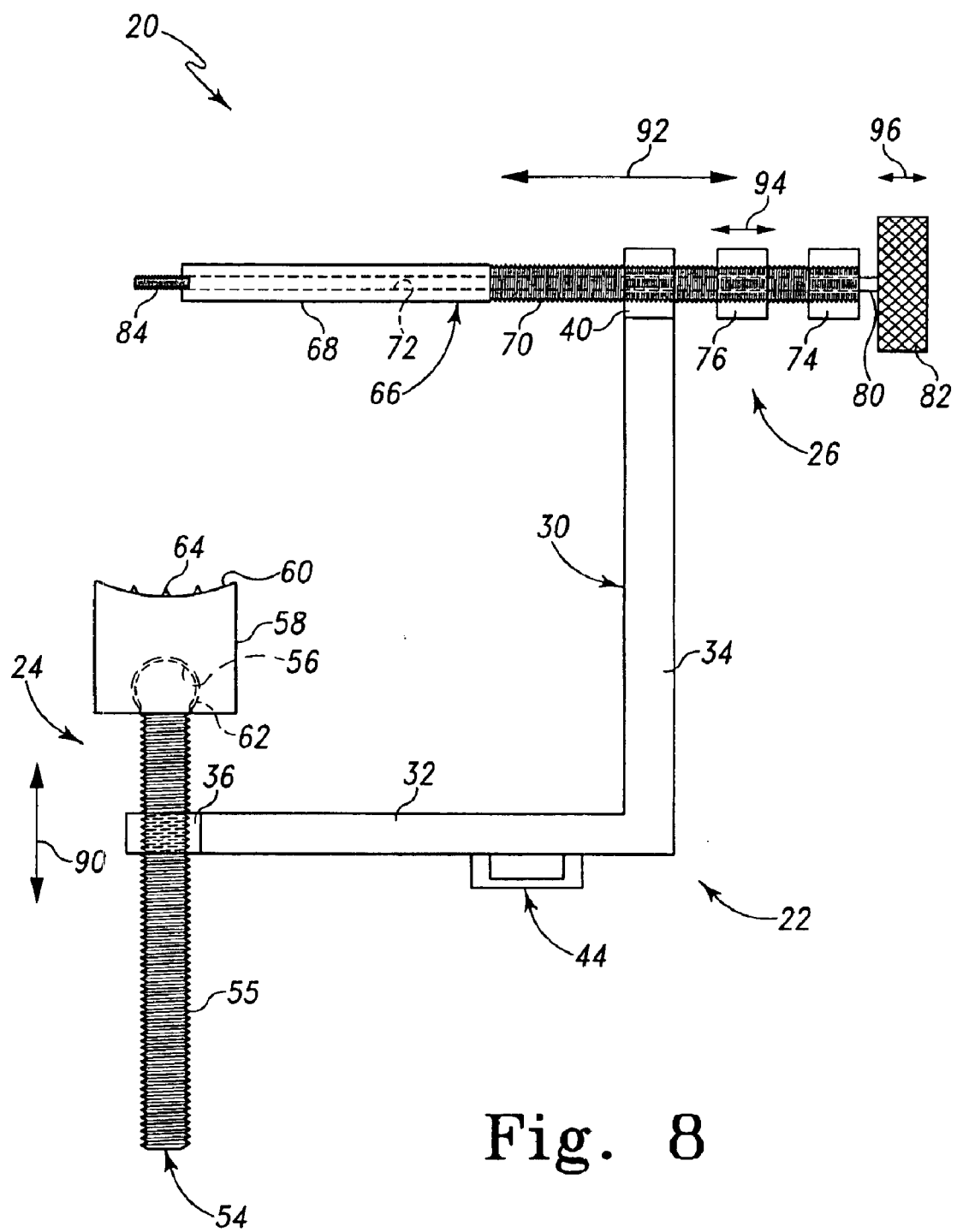
FIG. 8 is a top plan view of the exemplary bone resection guide of FIG. 1.

As shown in FIG. 1, the guide stem 54 is thus threadedly received in the threaded bore 38 of the eyelet 36. As such, the guide stem 54 is axially adjustable about the length of the threads 55 of the stem with respect to the eyelet 36. Therefore, in one direction of rotation of the guide stem 54, the guide stem 54 axially advances or moves toward an ulna (up and to the right in FIG. 1) and in another direction of rotation of the guide stem 54, the guide stem 54 axially advances or moves away from the ulna (down and to the left). Such translation of the guide stem 54 is represented by the arrow 90 in FIG. 8. Since the guide block 58 is coupled to or carried by the guide stem 54, the guide block 58 also advances towards or away from the ulna when the guide stem 54 is rotated in one direction and rotated in another direction. Again, such translation of the guide block 58 is represented by the arrow 90 in FIG. 8.

The guide block 58 includes a cavity 62 that is shaped in converse to the knob 56 and is therefore configured, adapted and/or operative to receive the knob 56. The knob 56 and the cavity 62 cooperate to allow the guide block 58 to pivot, rotate, swivel, or move about the knob 56. In this manner, the guide block 58 is positionable in an almost infinite number of positions with respect to the knob 56 and/or the guide shaft 54. In one form, the guide block 58 is formed of two components each of which includes a portion of the cavity 62 such that when the two components are coupled together with the knob 56 in therein, the knob 56 is captured in the cavity 62.

Figure 5:
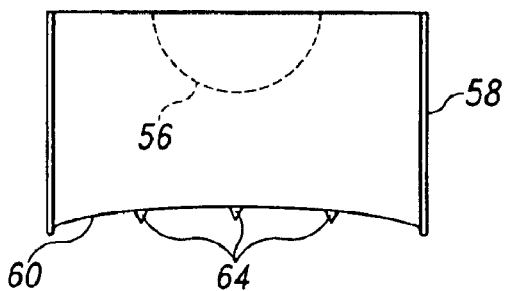
FIG. 5 is an enlarged, partial top view of an end of a guide block of the exemplary resection guide of FIG. 1.

The guide block has a front surface 60 that is rounded, curved or arcuate-shaped. Referring additionally to FIG. 5, a top view of the front surface 60 of the guide block 58 is seen. The curved front surface 60 preferably has a curvature that corresponds to a typical curvature of a posterior aspect of an olecranon of an ulna, but not necessarily. In addition, as best seen in FIG. 5, the front surface 60 includes a plurality of grips in the form of spikes 64. The spikes 64 allow the guide block 58 to be generally non-movably, but releasably, retained against the olecranon of the ulna during use. While three spikes 64 are shown, it should be appreciated that the number of spikes 64 is variable from one to many. As well, the height of each spike 64 may be the same or different than that of the other spikes. The overall and/or individual spike height may be variable.

Additionally, the bone resection guide 20 is contemplated for use with guide blocks of various sizes. Particularly, while a guide block 58 of only one size is used at a particular time (i.e. for a particular resection procedure), the bone resection guide 20 can use a different guide block 58 for each resection procedure. The various sizes of guide blocks 58 correspond to various sizes of olecranons. The guide blocks 58 may be provided in useful increments so that a useful range of sizes of guide blocks 58 is provided with the bone resection guide 20. The same guide shaft 54 may be used or different guide shafts 54 each having a different sized knob 56 may be provided for each different size guide block 58. Of course, with different sizes of knobs 56, each different sized guide block 58 would have a different cavity 62 to accommodate the different sized knob 56.

Further, rather than provide a range of sizes of guide blocks 58, two or more guide blocks 58 may be provided each of which has a front surface 60 of a different rate of curvature or arc. This may also provide accommodation to different sizes of olecranons. Even further, it is also contemplated that various combinations of different sizes of guide blocks and/or different rates of curvatures, and/or number of spikes may be used.

Figure 6:
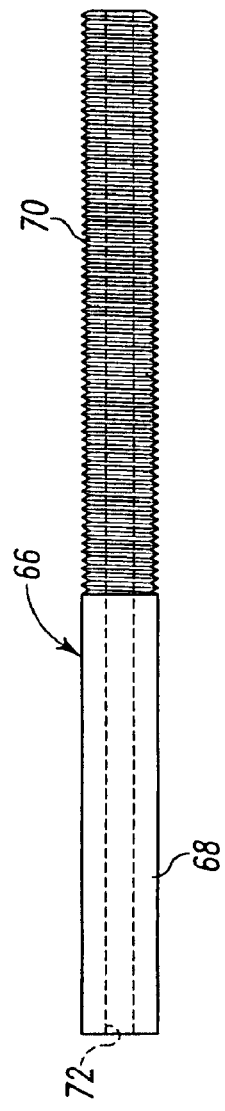
FIG. 6 is an enlarged plan view of a spool peg of the exemplary bone resection guide of FIG. 1.
Figure 7:
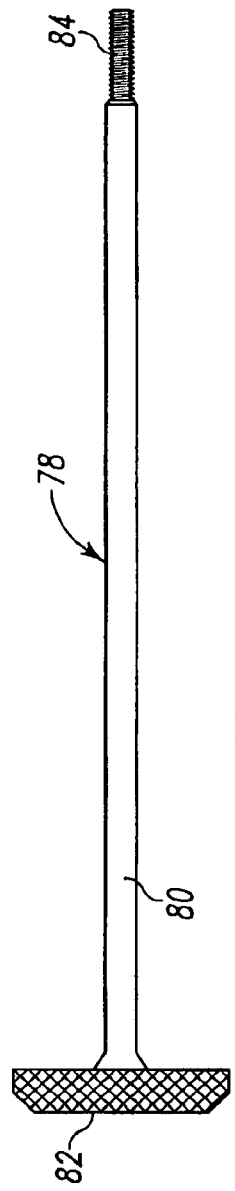
FIG. 7 is an enlarged plan view of a resection template mounting screw.

Referring back to FIG. 1, the resection spool/mock trochlea retention and adjustment assembly 26 of the resection guide 20 will be discussed. The resection spool/mock trochlea retention and adjustment assembly 26 is configured, adapted and/or operative to releasably retain a spool/mock trochlea 100 (the details of which are discussed below) in a trochlear notch of the ulna when the bone resection guide 20 is installed. The resection spool/mock trochlea retention and adjustment assembly 26 generally includes a spool peg 66, and a resection template mounting screw 78. The resection template mounting screw 78 extends through the spool peg 66 as described further below. The spool peg 66 is adjustable with respect to the guide frame 30, particularly with respect to the second leg 34. With additional reference to FIG. 6, the spool peg 66 is shown. The spool peg 66 includes threads 70 on a portion thereof, and a non-threaded portion 68 adjacent the threads 70. The spool peg 66 also has an internal bore 72 that extends axially or longitudinally therethrough. With additional reference to FIG. 7, the resection template mounting screw 78 is shown. The resection template mounting screw 78 includes a non-threaded shaft 80 having a knob 82 on one end thereof and a threaded portion 84 on another end thereof. The rounded outside edge of the knob 82 is preferably knurled to provide gripping power during use and/or setup of the subject bone resection guide 20. The diameter of the shaft 80 and threaded portion 84 is less than the diameter of the axial bore 72 of the spool peg 66 in order for the threaded portion 84 and the shaft 80 of the resection template mounting screw 78 to extend therethrough.

As shown in FIG. 1, the threaded portion 70 of the spool peg 66 is thus threadedly received in the threaded bore 42 of the eyelet 40. As such, the spool peg 66 is axially adjustable about the length of the threads 70 of the stem with respect to the eyelet 40 and a nut 76 movably, threadedly retained on the threaded portion 70. Therefore, in one direction of rotation of the spool peg 66, the spool peg 66 axially advances or moves essentially perpendicularly toward an ulna (to the left in FIG. 1) and in another direction of rotation of the spool peg 66, the spool peg 66 axially advances or moves perpendicularly away from the ulna (to the left). Such translation of the spool peg 66 is represented by the arrow 92 in FIG. 8. Since the resection template mounting screw 78 is coupled carried by the spool peg 66, the resection template mounting screw 78 also advances perpendicularly towards or away from the ulna when the spool peg 66 is rotated in one direction and rotated in another direction. Again, such translation of the resection template mounting screw 78 is represented by the arrow 96 in FIG. 8. The resection spool/mock trochlea retention and adjustment assembly 26 particularly is configured, adapted and/or operative to advance toward or away from the trochlear notch of the ulna in order to receive and releasably retain a spool or mock trochlea 100 of which is described below. The resection template mounting screw 78 is axially free within the bore 72 of the spool peg 68.

An end nut 74 is fixed on the threads 70 at the end of the spool peg 66. The fixed end nut 74 provides a stop for axial movement of the spool peg 66 through rotation that causes movement towards the ulna. Movement in the opposite direction via opposite rotation allows the resection spool/mock trochlea retention and adjustment assembly 26 to be removed from the eyelet 40 and thus the guide frame 30. An adjustment nut 76 is provided on the threaded portion 70 of the spool peg 66 between the eyelet 40 and the end nut 74. The adjustment nut 76 is freely movable between the eyelet 40 and the end nut 74 as indicated by the arrow 94 in FIG. 8. The adjustment nut 76 provides a limiting of the axial travel of the spool peg 66, through rotation thereof in cooperation with the threaded bore 42 of the eyelet 40, axially towards the ulna. In other words, the adjustment nut 76 adjustably limits the axial travel of the spool peg 66 in the axial direction towards the ulna. When the adjustment nut 76 is flush or immediately adjacent the end nut 74 the spool peg 66 is allowed to axially travel the greatest distance toward the ulna (maximum travel mode). When the adjustment nut 76 is at the end of the threaded portion 70 distal the end nut 74, the spool peg 66 is allowed to axially travel the least distance toward the ulna (least travel mode). In all cases, the spool peg 66 provides a seating means for and alignment of a spool or mock trochlea within the trochlear notch of the ulna.

Figure 9:
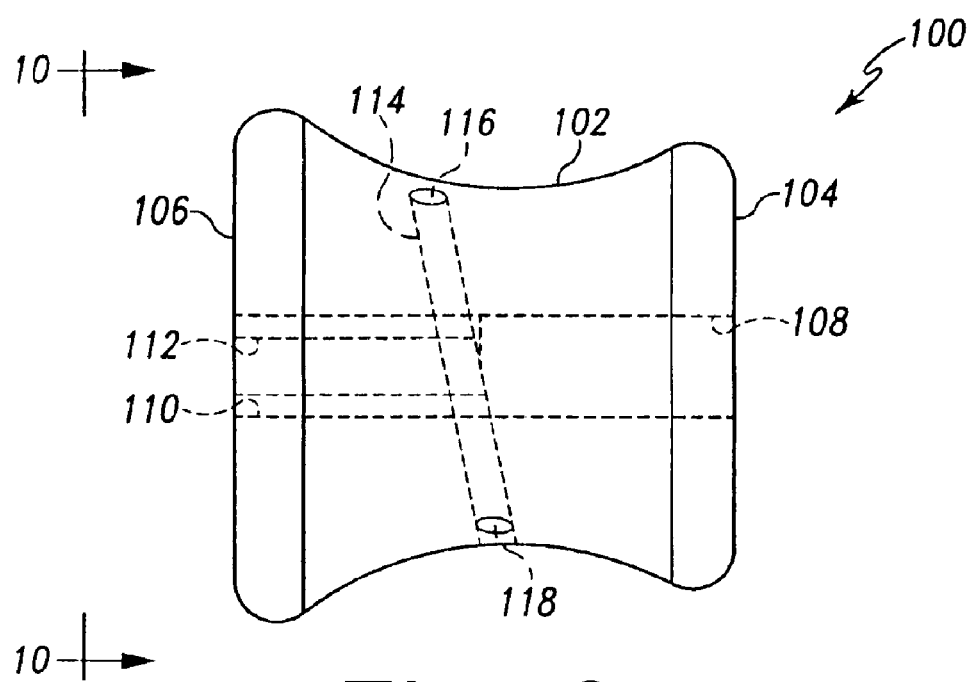
FIG. 9 is a side view of one size of an exemplary spool/mock trochlea for the exemplary bone resection guide of FIG. 1.
Figure 10:
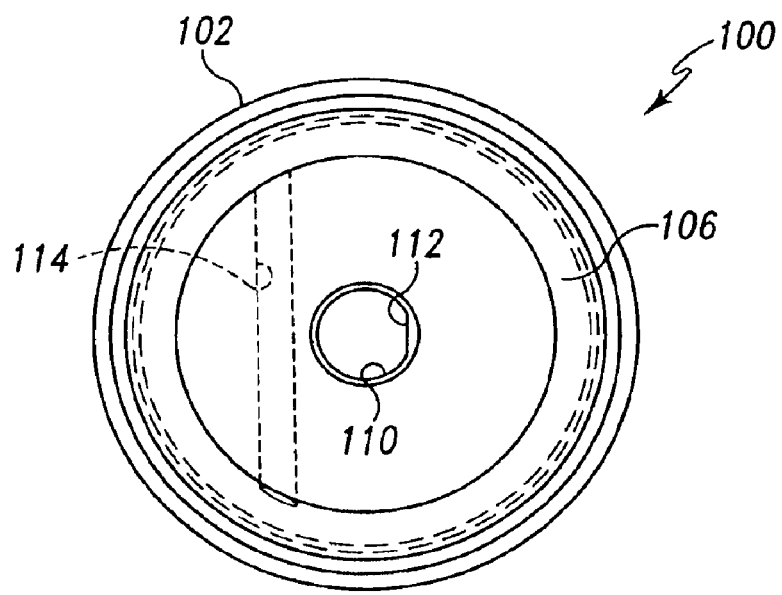
FIG. 10 is a side view of the exemplary spool/mock trochlea taken along line 10—10 of FIG. 9.

Referring to FIGS. 9 and 10, there is depicted an exemplary spool, bobbin, mock trochlea, or the like generally designated 100 (and hereinafter, collectively "spool"). The spool 100 is defined by a saddle-shaped body 102 having a first end 104 and a second end 106. It should be appreciated that the nomenclature "first" and "second" are arbitrary and thus may be interchanged without consequence. The body 102 is shaped to simulate the trochlea of the humerus. As such, in accordance with an aspect of the subject invention, the spool 100 is provided in various sizes, preferably in useful increments or incremental sizes. Since each spool is identical except for size, hereinafter, the characteristics of the spool 100 is intended to cover each and every spool.

The spool 100 has a first bore 108 extending axially into the body 102 from the first end 104. The first bore 108 is sized to receive the non-threaded portion 68 of the spool peg (see, e.g. FIGS. 11 and 12). The first bore 108 extends substantially mid or half-way axially into the body 102. A second bore 110 extends axially into the body 102 from the second end 106. The second bore 110 extends substantially mid or half-way axially into the body 102. As best seen in FIG. 10, the second bore 110 has a flat 112 that axially extends the distance of the second bore 110. The flat 112 essentially creates a "D" shaped profile for the second bore 110. As described below, the second bore 110 is configured, adapted, and/or operative to receive an orientation rod of a resection template. The first and second bores 108 and 110 are in axial communication with each other.

The spool 100 also includes a skewed bore 114 defining an opening 116 on one side of the body 102 and an opening 118 on another side of the body 102. The bore 114 essentially defines a chord as best depicted in FIG. 10. The bore 114 is sized to receive a spool retention rod therethrough. As described below, the spool retention rod allows the spool 100 to be temporarily fixed in the trochlear notch of the ulna. The rod also aligns the axis of the spool at 10 degrees from the long axis of the ulna (this is the angle the prosthesis is designed at) when the rod is oriented parallel to the long axis of the ulna.

Figure 11:
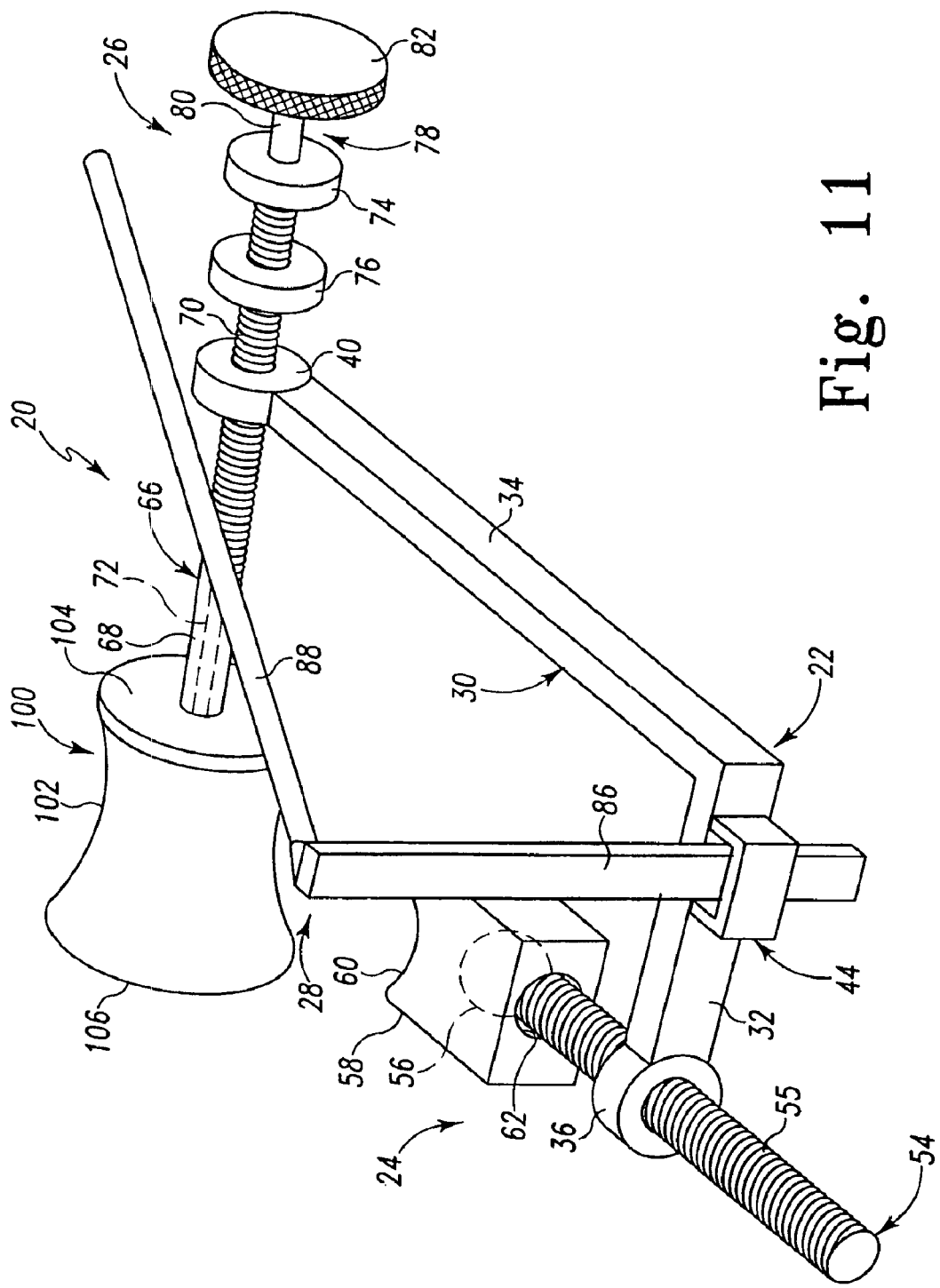
FIG. 11 is a perspective view of the exemplary bone resection guide of FIG. 1 with one size of an exemplary spool/mock trochlea attached thereto.
Figure 12:
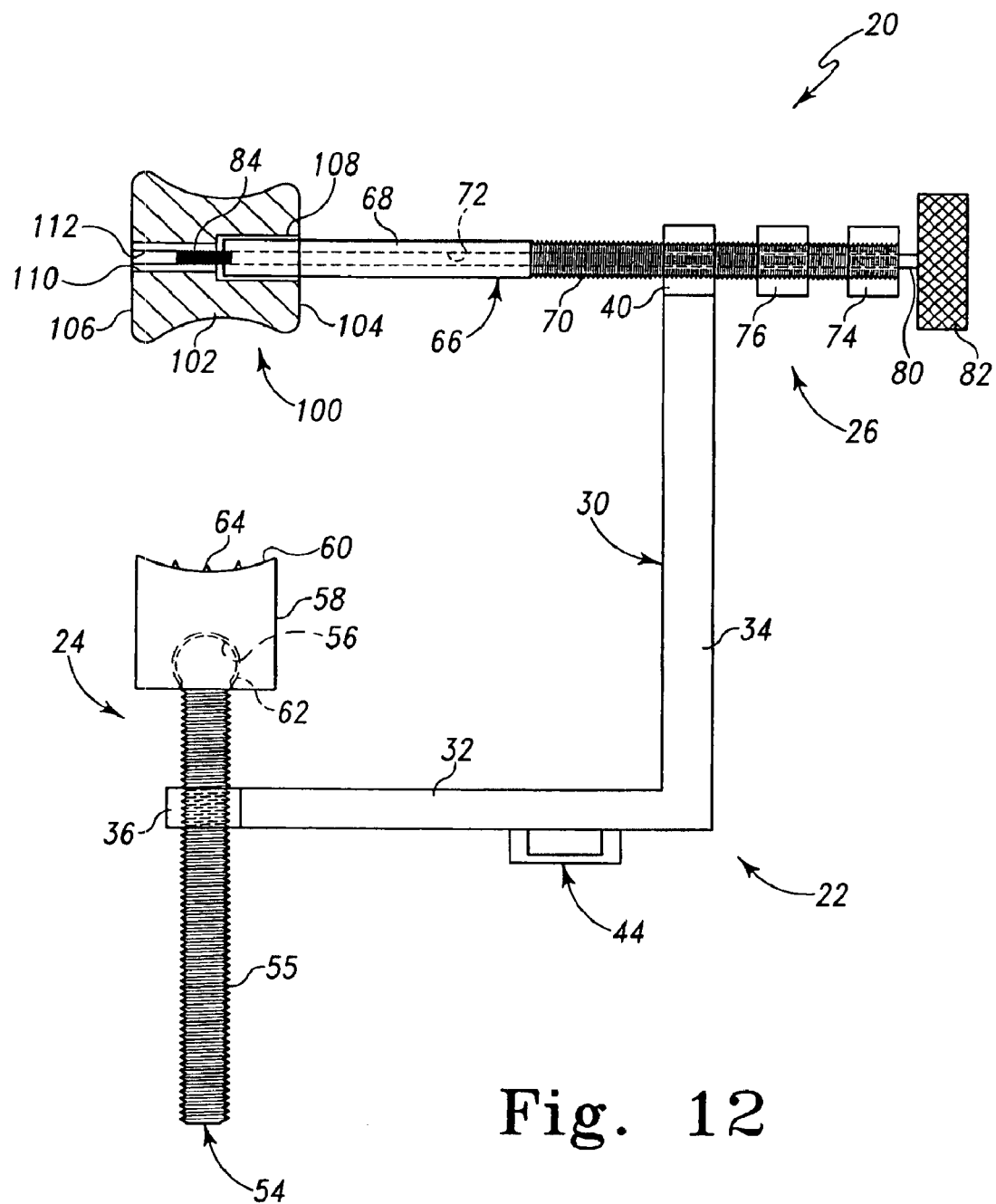
FIG. 12 is a top plan view of the exemplary bone resection guide of FIG. 1 with one size of an exemplary spool/mock trochlea attached thereto shown in sectional.

Referring to FIGS. 11 and 12, a spool 100 of an appropriate size of one of the various-dimensioned (sizes and/or shapes) spools 100 is shown situated on the spool peg 66. It should be appreciated that the resection guide assembly 20 is typically not attached to the spool 100 without the appropriately size-chosen spool 100 being previously situated in the trochlear notch of a patient's ulna. The spool 100, however, is shown mounted onto the spool peg 66 for purposes of illustration of the manner in which the resection guide assembly 20 and the spools join.

Referring particularly to FIG. 12, a spool 100 is shown in sectional view mounted on the spool peg 66. Stated another way, the spool peg 66 of the resection guide assembly 20 is shown in engagement with the spool 100 after the appropriately-sized spool has been chosen and is situated in the trochlear notch of the patient's ulna in preparation for resection of the ulna in preparation for prosthetic implantation. When the appropriate sized spool placed in the proper location within the ulnar trochlear notch, the axis of the spool substantially estimates the rotation axis of the ulna. The end of the non-threaded portion 68 of the spool peg 66 is received in the first bore 108. The threaded end or tip 84 of the resection template mounting or retention screw 78 extends from the end of the spool peg 66 into the second bore 110. The threaded end 84 is ready to receive and releasably retain a resection template.

Figures 13, 14:
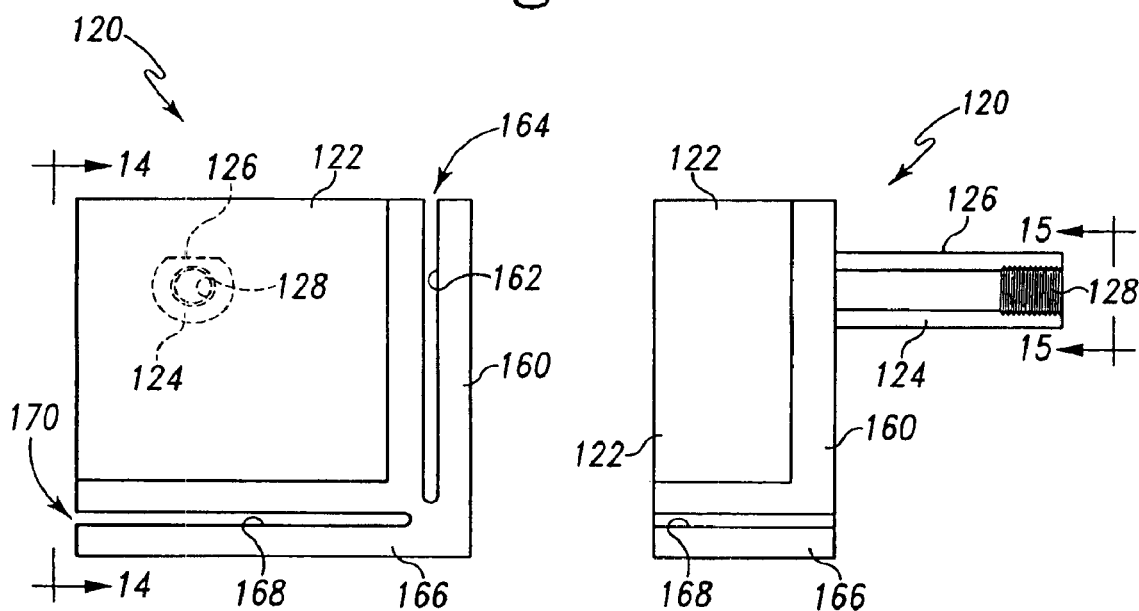
FIG. 13 is a front view of one size of an exemplary resection guide template for the exemplary bone resection guide of FIG. 1.
FIG. 14 is a side view of the exemplary resection guide template for the exemplary bone resection guide taken along line 14—14 of FIG. 13.
Figure 15:
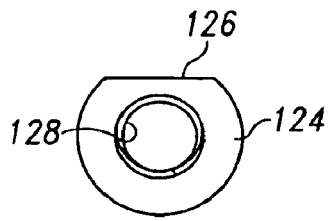
FIG. 15 is a side view of the mounting rod of the exemplary resection guide template for the exemplary bone resection guide taken along line 15—15 of FIG. 14.

Referring now to FIGS. 13–15, an exemplary resection template, generally designated 120, is shown. The exemplary resection template 120 includes a substantially flat plate 122 with a first transverse wall 160 on one edge of the plate 122 and a second transverse wall 166 on another edge of the plate 122. The first and second transverse walls 160 and 166 have a common edge. The first transverse wall 160 has a slot 162 formed therein that has an opening 164 on one end of the first transverse wall 160. The slot 162 provides a guide for a cutting instrument (such as a bone saw) for resection of ulna bone. The cutting instrument enters the slot 162 via the opening 164, while the slot 162 provides a guide for the cutting instrument and hence resection. The second transverse wall 166 has a slot 168 formed therein that has an opening 170 on one end of the second transverse wall 166. The slot 168 provides a guide for a cutting instrument (such as a bone saw) for resection of ulna bone. The cutting instrument enters the slot 168 via the opening 170, while the slot 168 provides a guide for the cutting instrument and hence resection.

The resection guide 120 further has a mounting rod 124 extending from a side thereof. The mounting rod 124 includes a flat 126 that defines a "D" cross-section to the rod 124. The D-shaped mounting rod 124 thus corresponds in shape with the D-shaped bore 110 of the spool. This provides a specific orientation for the resection template with respect to the spool 100. The rod 124 also includes a threaded bore 128 that is sized to threadedly receive the threaded end 84 of the resection template mounting screw 78. According to an aspect of the subject invention, various dimensions (sizes and/or shapes) of resection templates are provided in order to accommodate various sizes of ulnas to be resected and/or various implant sizes.

Figure 16:
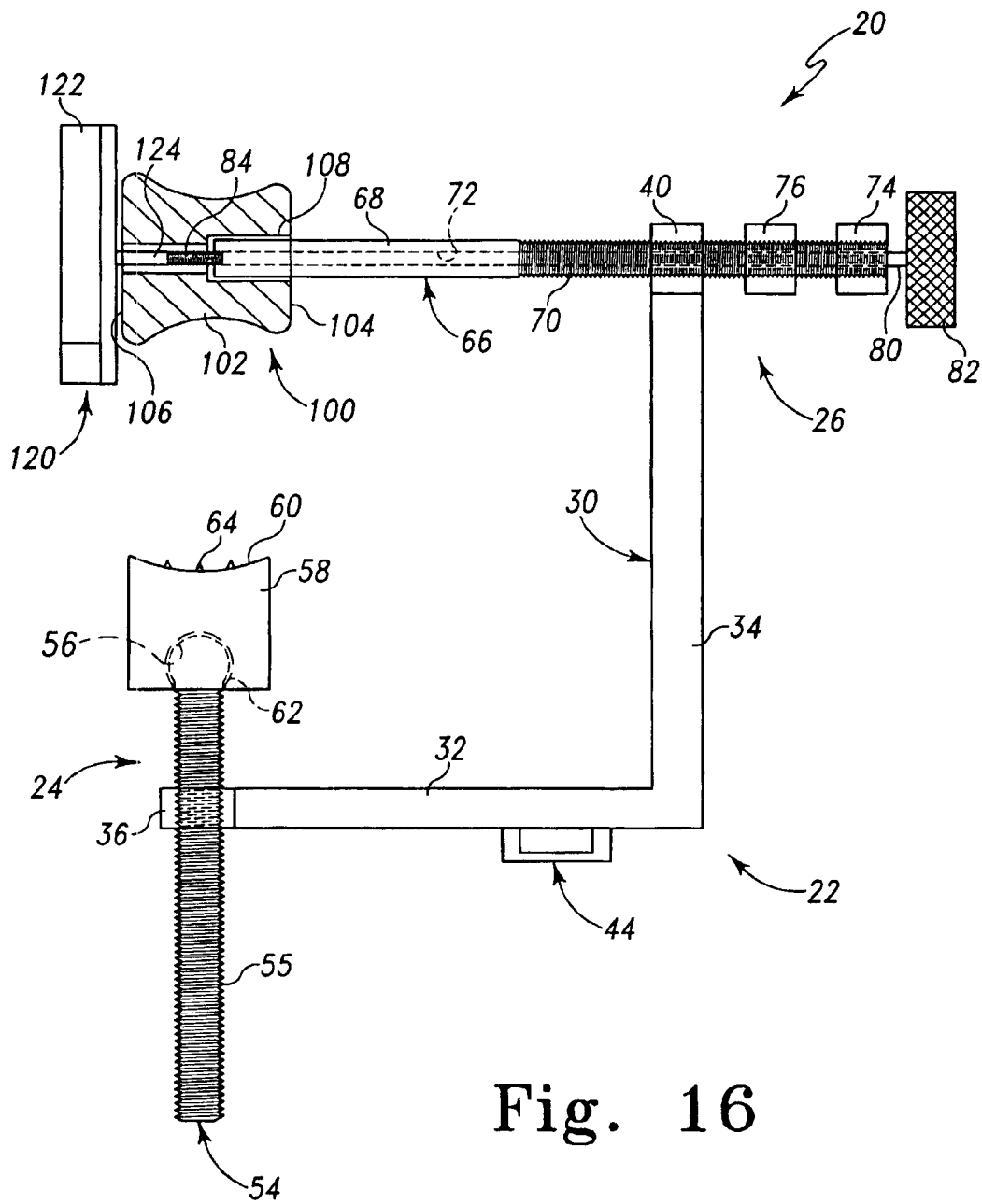
FIG. 16 is a top plan view of the exemplary bone resection guide of FIG. 1 with one size of an exemplary spool/mock trochlea attached thereto shown in sectional with one size of an exemplary resection guide template attached thereto.

Referring to FIG. 16, a resection template 120 of an appropriate size of one of the various-sized resection templates 120 is shown situated on the spool 100 and the threaded end 84 of the resection template mounting screw 78. Particularly, the shaft 124 of the resection template 120 is within the bore 110, while the threaded end 84 of the resection template mounting screw 78, via rotation of the knurled knob 82 is threadedly engaged or received in the threaded bore 128 of the shaft 124. It should be appreciated that the resection template 120 is typically not received in the spool 100 without the appropriately size-chosen spool 100 being previously situated in the trochlear notch of a patient's ulna, the resection guide 20 attached thereto, and a spool retention rod extending through the bore 114 and into the ulna. The resection template 120, however, is shown mounted onto the spool 100 for purposes of illustration of the manner in which the resection template 120 and the spool 100 join.

Use of the Subject Invention

Figure 17:
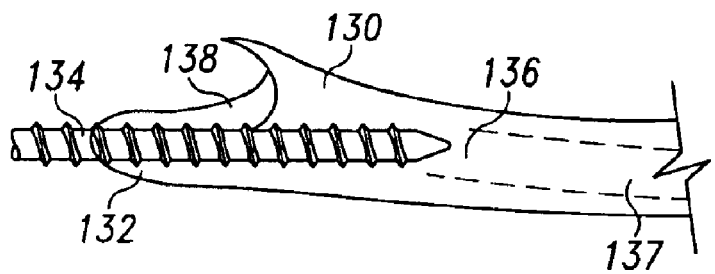
FIG. 17 is a side view of an ulna being initially prepared for soft tissue balance.
Figure 18:
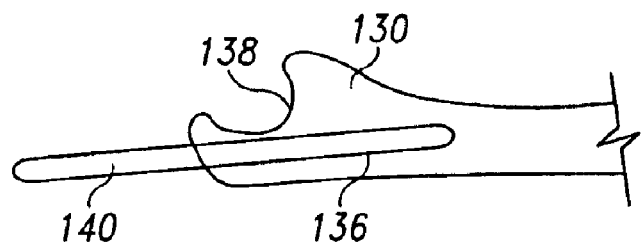
FIG. 18 is a side view of the ulna with an intramedullary rod in the prepared ulna.
Figure 19:
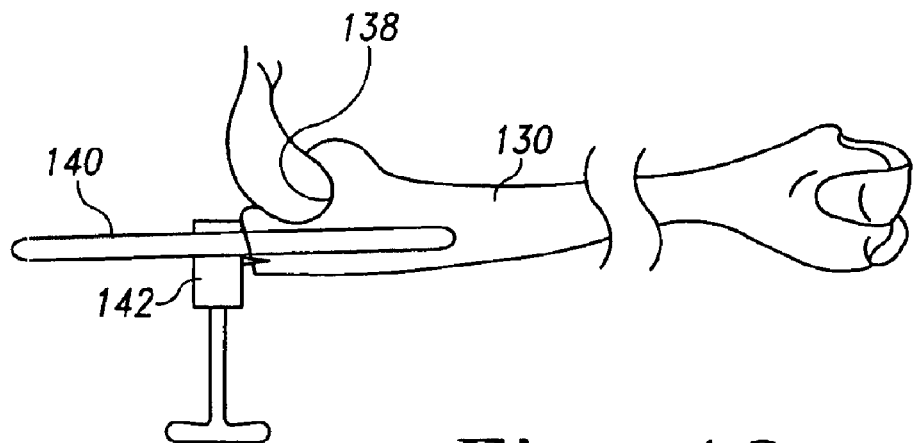
FIG. 19 is a side view of the ulna undergoing soft tissue balance.

A use and/or application of the subject invention will now be described. It should be appreciated, however, that the below-described use/application of the subject invention is only exemplary of one manner of use. Other manners of use not specifically described herein are contemplated. Referring to FIG. 17, there is depicted a section of an ulna 130 particularly the end of the ulna 130 with the olecranon 132 and the trochlear notch 138 (i.e. the elbow). The ulna 130 will be resected for prosthetic implant. It should initially be appreciated that the procedure described herein with respect to FIGS. 17–19 are not necessary for use of the subject resection guide, but are optional.

In FIG. 17, the ulna is initially prepared by reaming a bore 136 in the medullary canal 137 of the ulna by a reamer 134. Thereafter, as depicted in FIG. 18, an intramedullary rod 140 is placed in the reamed bore 136. Once the intramedullary rod 140 is in place, a grasper 142 is attached to the intramedullary rod 140 as depicted in FIG. 19. At this point soft tissue balance may be determined, and an estimation of the optimum axis of rotation can be made.

Figure 20:
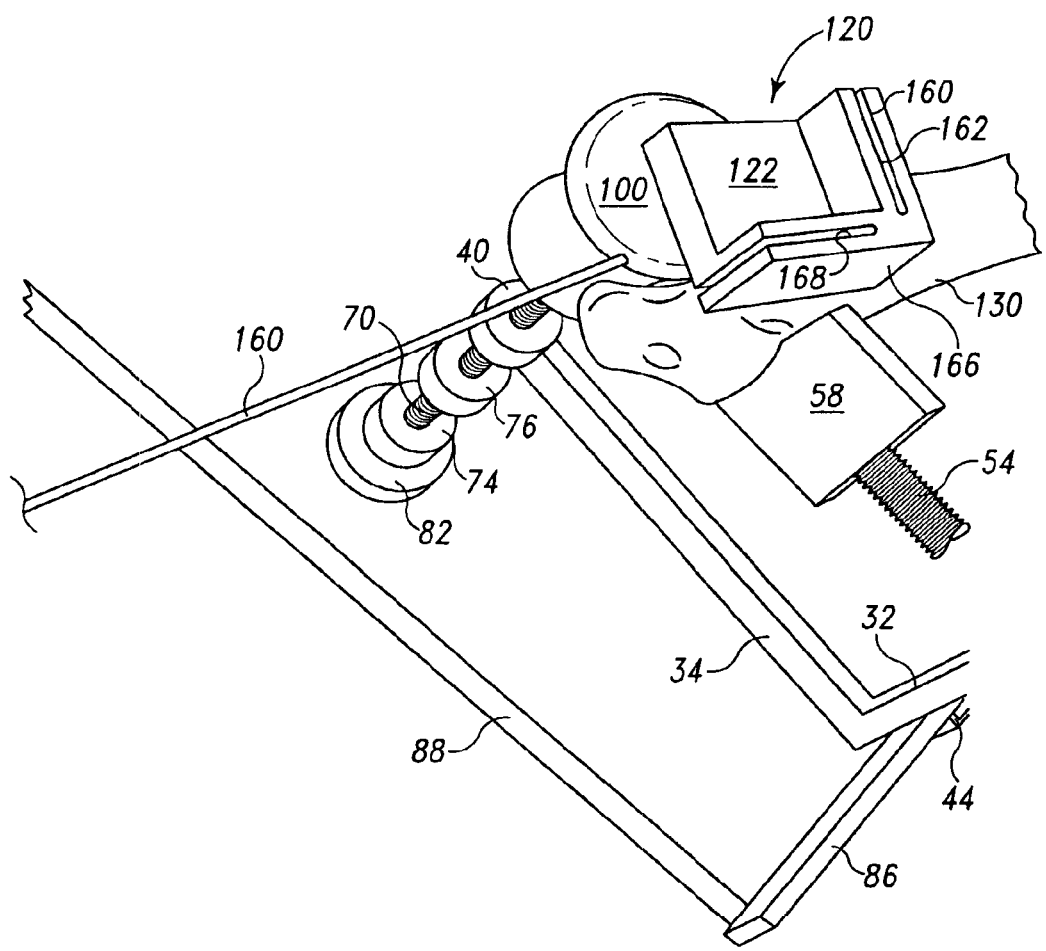
FIG. 20 is a perspective view of a spool, resection guide template, and bone resection guide assembly in position with respect to an ulna.

Further, and in preparation of resection of a portion or more of the olecranon 132, an appropriate dimensioned spool or mock trochlea 100 is selected and placed in the olecranon 132. Thereafter, and with reference to FIG. 20, the bone resection guide assembly 20 is shown in an appropriate position. Particularly, the resection guide assembly is appropriately adjusted with the block 58 bearing against the olecranon 132, the spool 100 is retained by the guide assembly 26, a trocar-tipped pin 160 is retaining the spool 100, and an appropriate resection template 120 is placed on the spool 100. The trocar-tipped pin 160 preferably extends into the ulna 130.

Once the resection guide 20, the appropriate spool 100, and an appropriate resection template 120 is appropriately situated, a bone cutting instrument such as a bone saw (not shown) is used to cut ulna bone. Particularly, the cutting instrument uses the slots 162 and 168 to resect an appropriate portion of the ulna. This provides a properly resected ulna for the particular prosthesis.

There are a plurality of advantages of the subject invention arising from the various features of the resection guide assembly described herein. It will be noted that alternative embodiments of the resection guide assembly of the subject invention may not include all of the features described yet still benefit from at least some of the advantages of such features. Those of ordinary skill in the art may readily devise their own implementations of a resection guide assembly that incorporate one or more of the features of the subject invention and fall within the sprit and scope of the subject invention.

What is claimed is:

1. A bone resection guide for an ulna comprising:
    a frame;
    a guide block adjustably carried by said frame and operative to contact an olecrannon of an ulna of a patient; and
    a mock trochlea holder adjustably carried by said frame and operative to temporarily retain a selected mock trochlea in a trochlear notch of the ulna of the patient,
    wherein said guide block comprises: (i) a guide stem adjustabty coupled to said frame; and (ii) a guide block coupled to an end of said guide stem.

2. The bone resection guide of claim 1, wherein said guide block is coupled to said guide stem for pivotal motion.

3. The bone resection guide of claim 1, wherein said guide block includes a curved front surface adapted to contact the olecranon of the ulna.

4. The bone resection guide of claim 3, wherein said curved front surface has a plurality of spikes.

5. The bone resection guide of claim 1, wherein said guide stem is threaded, said frame includes a first threaded bore, and said threaded guide stem is threadedly received in said first threaded bore.

6. The bone resection guide of claim 1, wherein said mock trochlea holder is further configured to retain a selected resection template onto the mock trochlea.

7. The bone resection guide of claim 1, wherein said mock trochlea holder comprises:
    a mock trochlea peg adjustably coupled to said frame; and
    a resection template screw carried by said mock trochlea peg.

8. The bone resection guide of claim 7, wherein said mock trochlea peg is threaded, said frame includes a second threaded bore, and said mock trochlea peg is threadedly received in said second threaded bore.

9. The bone resection guide of claim 7, wherein said mock trochlea holder is operative to temporarily axially retain a selected mock trochlea in a trochlear notch of the ulna of the patient.

10. The bone resection guide of claim 9, wherein said mock trochlea holder includes an adjustment device operative to adjust an axial length of travel of said mock trochlea peg.

11. The bone resection guide of claim 1, further comprising:
    an axis finder/locator carried by said frame, said axis finder configured to indicate a pivot axis of the ulna and a humerus of the patient.

12. A method of preparing an ulna for prosthetic implantation comprising the steps of:
    determining a reference axis of natural elbow rotation of an elbow of a patient with respect to an ulna of the elbow, said determining step including (i) placing a selected mock trochlea into a trochlear notch of an ulna of a patient, and (ii) temporarily fixing the mock trochlea within the trochlear notch of the ulna;
    selecting a template having a plurality of resection guide surfaces from one of a plurality of templates having various dimensions and resection guide surfaces;
    situating the selected template adjacent the ulna and with respect to the determined reference axis; and
    resecting a portion of the ulna according to the resection guide surfaces while the selected mock trochlea is fixed within the trochlear notch of the ulna of the patient.

13. The method of claim 12, wherein said determining step further includes the step of:
    mating an elbow axis locator to a particular size of an ulna fossa of the ulna.

14. The method of claim 13, wherein the step of placing a selected mock trochlea into a trochlear notch of an ulna includes the step of selecting a mock trochlea from a plurality of mock trochleas of different dimensions before placing the selected mock trochlea into a trochlear notch of an ulna.

15. The method of claim 14, wherein the step of selecting a mock trochlea from a plurality of mock trochleas of different dimensions before placing the selected mock trochlea into a trochlear notch of an ulna includes the step of matching a mock trochlea of a particular dimension to a trochlea of the patient.

16. The method of claim 12, wherein the step of selecting a template having a plurality of resection guide surfaces from one of a plurality of templates having various dimensions and resection guide surfaces includes the step of matching a template size to an olecranon of the patient or a prosthesis to be implanted in the patient.

17. The method of claim 12, wherein the step of temporarily fixing the mock trochlea in the trochlear notch of the ulna includes the step of temporarily axially retaining the mock trochlea.

18. The method of claim 12, wherein the step of temporarily fixing the mock trochlea in the trochlear notch of the ulna includes the step of temporarily radially retaining the mock trochlea.

19. A method of preparing a bone for prosthetic implantation comprising the steps of:
placing a selected mock trochlea into a trochlear notch of an ulna of a patient;
temporarily fixing the mock trochlea in the trochlear notch;
placing a selected resection template onto the mock trochlea; and
resecting bone from the ulna according to the resection template.

20. The method of claim 19, wherein the step of placing a selected mock trochlea into a trochlear notch of an ulna includes the step of selecting a mock trochlea from a plurality of mock trochleas of various dimensions before placing the selected mock trochlea into a trochlear notch of an ulna.

21. The method of claim 20, wherein the step of selecting a mock trochlea from a plurality of mock trochleas of various dimensions before placing the selected mock trochlea into a trochlear notch of an ulna includes the step of matching a mock trochlea size from the plurality of mock trochleas of various dimensions to a trochlea of the patient.

22. The method of claim 20, wherein the step of placing a selected resection template onto the mock trochlea includes the step of selecting a resection template from a plurality of resection templates of various dimensions and resection guide surfaces.

23. The method of claim 22, wherein the step of selecting a resection template from a plurality of resection templates of various dimensions and resection guide surfaces includes the step of matching a template size of the plurality of templates to an olecranon of the patient or a prosthesis to be implanted in the patient.

24. The method of claim 19, wherein the step of temporarily fixing the mock trochlea in the trochlear notch of the ulna includes the step of aligning the mock trochlea to a natural axis of elbow rotation of the patient.

25. The method of claim 19, wherein the step of temporarily fixing the mock trochlea in the trochlear notch of the ulna includes the step of temporarily axially retaining the mock trochlea.

26. The method of claim 19, wherein the step of temporarily fixing the mock trochlea in the trochlear notch of the ulna includes the step of temporarily radially retaining the mock trochlea.

27. The method of claim 19, wherein said resecting step includes the step of resecting bone from the ulna according to the resection template while the mock trochlea is fixed within the trochlear notch.

* * * * *